United States Patent [19]

Rühland

[11] Patent Number: 4,564,359
[45] Date of Patent: Jan. 14, 1986

[54] AUTOTRANSFUSION APPARATUS'

[76] Inventor: Dieter Rühland, Jungeblodtplatz 1, 4400 Münster, Del.X

[21] Appl. No.: 576,673

[22] Filed: Feb. 3, 1984

[30] Foreign Application Priority Data

Feb. 10, 1983 [DE] Fed. Rep. of Germany ....... 3304486

[51] Int. Cl.$^4$ .......................... A61M 1/02; A61M 5/14
[52] U.S. Cl. ................................. 604/4; 128/DIG. 3; 422/44; 604/319; 604/320; 604/321
[58] Field of Search ................... 604/4, 5, 6, 319–321; 128/DIG. 3; 422/44

[56] References Cited

U.S. PATENT DOCUMENTS

| | | | |
|---|---|---|---|
| 3,993,067 | 11/1976 | Schachet et al. | 604/4 |
| 4,006,745 | 2/1977 | Sorrenson et al. | 604/4 |
| 4,014,329 | 3/1977 | Welch et al. | 128/214 R |
| 4,033,345 | 7/1977 | Sorenson et al. | 128/214 R |
| 4,047,526 | 9/1977 | Reynolds et al. | 128/214 R |
| 4,111,204 | 9/1978 | Hessel | 604/321 |

FOREIGN PATENT DOCUMENTS 3218561  11/1983  Fed. Rep. of Germany .

Primary Examiner—Curtis R. Davis
Attorney, Agent, or Firm—Martin A. Farber

[57] ABSTRACT

An autotransfusion apparatus for blood or a similar body fluid, comprising
(a) an evacuatable vacuum-resistant container (5) having a bottom part (4) and a cover part (3), with
  (a1) an inlet opening (20) for the body fluid arranged in the cover part,
  (a2) an outlet opening (24) for the body fluid having a screen (25) covering the outlet opening, and
  (a3) an opening (9) for producing a gas-flow connection to a space having a gas pressure which differs from the inside of the container. The blood can be collected in a short path without damage and transfused it rapidly back into the patient with dependable fractionality and without injuring the patient, by
(b) the outlet opening (24) also being arranged in the cover part (3),
(c) the opening (9) being arranged in the bottom part (4), and
(d) a membrane (16) which is deformable by pressure and impervious to the body fluid
  (d1) is held fast hermetically on its edge between the bottom and cover parts,
  (d2) divides the container (5) into a gas-filled bottom space (13) and a cover space (19), sealed off from the former, to receive the body fluid, and
  (d3) can be applied under the influence of a fluid pressure, substantially, both against the inner contour (1) of the cover part (3) or respectively against the inner contour (2) of the bottom part (4).

20 Claims, 5 Drawing Figures

AUTOTRANSFUSION APPARATUS'

FIELD AND BACKGROUND OF THE INVENTION

The present invention relates to an autotransfusion apparatus for blood or similar body fluid. Such an apparatus comprises:
- (a) an evacuatable, vacuum-resistant container having a bottom part and a cover part, with
  - (a1) an inlet opening for the body fluid arranged in the cover part,
  - (a2) an outlet opening for the body fluid having a screen which covers the outlet opening, and
  - (a3) an opening to produce a gas-flow connection to a space having a gas pressure which differs from the inside of the container.

In surgical operations, for instance in the fields of heart surgery, vascular surgery, accident surgery and orthopedics, there are frequently large, rapid losses of blood which today are generally still compensated for by donor blood. Donor blood, however, may transmit disease (for instance, hepatitis). Furthermore, donor blood which is frequently several weeks old lacks the coagulation elements (coagulation factors and blood platelets), which have been destroyed by storage. It is therefore urgently necessary to have apparatus available which is adapted to recover the blood which collects in the body cavities during an operation and return it to the patient in order to reduce the use of donor blood and substantially retain the blood coagulation elements.

THE PRIOR ART

For the recovery of the patient's own blood (autotransfusion) for major heart operations, complicated and expensive heart-lung machines are available today which draw the blood of the patient off via a pump mechanism and then return it through long tubes. Other apparatus collect the blood fluid, isolate and wash the red blood cells, and return these washed blood cells to the body. In both of these apparatus the sensitive blood cells are damaged by long suction paths (surface contact), while in the second apparatus all coagulation elements and the blood plasma are removed by the washing process. These apparatus are furthermore extremely expensive and therefore available only at a few centers.

Other apparatus have therefore been developed for intra-operative autotransfusion. Thus U.S. Pat. No. 4,047,526 discloses an autotransfusion apparatus of the afore mentioned type in which the blood is first of all collected in a rigid container under vacuum and then transferred into a foldable bellows which is detachably connected to the bottom of the rigid collecting container, the bellows being capable of forming a vacuum which can overcome the vacuum in the rigid container lying above it. The blood-filled bellows are then detached from the rigid container and then used for the active retransfusion of the blood.

U.S. Pat. No. 4,033,345 describes a different embodiment of an autotransfusion apparatus having a rigid two-chamber system which contains an inner, deformable bag which is connected by a one-way valve to the upper chamber, which initially collects the blood. The blood can be actively transfused back into the patient through another opening with one-way valve and filter units as a result of the entrance of a fluid under pressure into the space between the rigid second chamber and the outer surface of the bag. The transfer of the blood from the rigid collecting container into the flexible bag takes place by the alternate application of pressure and vacuum.

Another autotransfusion apparatus, known from the subsequently published Federal Republic of Germany Patent Application No. OS 32 18 561, is a device which corresponds to the second chamber of the above-mentioned U.S. Pat. No. 4,033,345 and in the case of which the blood must be drawn out, however without one-way valves, through an opening in the bottom of the chamber and in which neither a screen nor a similar blood filter can be used.

Finally, from U.S. Pat. No. 4,014,329 another two-chamber autotransfusion apparatus is known in which the first chamber operates in accordance with the same principle as has been described for the second chamber in U.S. Pat. No. 4,033,345; in this case, however, the blood flows by gravity from the bottom of the chamber into the second chamber with filter.

With these known autotransfusion apparatus it is possible, it is true, to collect blood which has accumulated intra-operatively and retransfuse it into the patient, but they have a number of definite disadvantages. With the multi-chamber systems, the blood comes into contact with a large surface of the apparatus, which causes a detrimental activating of coagulation and also traumatizing of the blood. Similarly, there is a further traumatizing—which is detrimental for the sensitive blood cells—upon the transfer from the one chamber into the other, particularly if one-way valves are present between the chambers. If the blood is drawn from below into the vacuum chamber, then the blood which has already accumulated in the apparatus is placed in turbulent movement by the blood which is successively drawn in, in which connection entrained air and coarse particles such as blood, coagulum, fat cells and bone splinters result in a considerable formation of foam as well as in a traumatizing of the blood cells. In the absence of coarse filters to retain substances carried along in the blood there is, finally, the latent danger of the clogging of the fine filters traditionally provided on the transfusion instruments. Furthermore, the blood collection chambers, which are provided with inlet and outlet openings on their top and bottom sides, must be of a considerable structural height in view of the amount of blood which must be drawn in, this height being, as a general rule, greater than the very small sterile operating field on the patient; accordingly, with the known autotransfusion apparatus sterilization problems in the sterile operating field regularly recur and they can only be counteracted by setting up the autotransfusion apparatus outside the sterile region and tolerating a longer suction path. Therefore, a higher suction pressure is necessary and increased foreign body contact is established, both of which mean additional trauma for the blood. In two-chamber systems the transfer of the blood after aspiration into the second chamber requires time, which is not available to the anesthetist nor to the surgeon in the event of a mass accumulation of blood; the time factor is, however, particularly detrimental also for the patient, since it is necessary to get his blood back again particularly quickly in this case.

Based on the above it is an object of the present invention to create a reliably functioning autotransfusion apparatus of the introductory-mentioned type with which it is possible to collect the blood over a short path without damage and to transfuse it rapidly back again into the patient, with reliable functionality and without the possibility of injury to the patient; in particular, the contact surfaces contacted by the blood should be as small as possible and narrow points as well as foaming avoided and a low structural height which permits use in the sterile region of the patient should be obtained.

SUMMARY OF THE INVENTION

Accordingly the present invention provides that:
(b) the outlet opening also be arranged in the cover part,
(c) the opening for gas pressure which differs from the inside of the container is arranged in the bottom part, and
(d) a pressure-deformable membrane which is impervious to the body fluid
   (d1) is hermetically fastened at its edge between the bottom and cover parts,
   (d2) divides the container into a gas-filled bottom space and a cover space, sealed from same, to receive the body fluid, and
   (d3) is adapted to be applied essentially both against the inner contour of the cover part and against the inner contour of the bottom part under the influence of a fluid pressure.

The invention, accordingly, starts out the basic concept of arranging both the blood inlet opening and the blood outlet opening, with a coarse filter in front of it, in the cover part of a single blood collection chamber so that the blood drawn in passes from above into this chamber and flows without foaming downward along the wall of the chamber; for retransfusion, the apparatus is turned upside down and the blood flows, filtered under the action of gravity and/or elevated gas pressure within the bottom space, which is separated by a membrane from the blood collection chamber, back to the patient; the previous drawing-in of the blood is, in this connection, effected by a vacuum which is applied either—in the case of a hermetically closed bottom space—to the outlet opening or, in the case of a hermetically closed outlet opening, within the bottom space; the membrane is, accordingly, secured merely on its edge between the bottom and the cover part, the ratio of the size of the bottom part to that of the cover part being immaterial, it being merely necessary to insure that the membrane can apply itself alternately as extensively as possible against the wall of both the bottom part and the cover part so that the bottom and the cover space alternately have a minimum residual volume.

Upon the use of vacuum in the cover space the inlet and outlet openings must be sufficiently far apart to prevent passage of blood into the applied source of vacuum.

The autotransfusion apparatus of the invention has a number of important advantages: The blood is collected in a single chamber without any constricting cross sections, without the formation of foam and under a controllable pressure and it is infused prefiltered directly into the patient from said chamber with all desired speed by the application of a freely determinable pressure; for this purpose only a very small structural height of the vacuum-resistant container is necessary, so that it can be handled at any time within the sterile region of the operation. Furthermore, sealing problems within the region of the three container openings and in connection with the membrane are avoided since these openings are all arranged in the substantially rigid wall of the cover part or bottom part, and therefore independently of the sealing edge of the membrane; therefore, it is merely necessary for the edge of the membrane to be fastened in the manner which is functionally best suited for this between the cover and bottom parts, and complete passage openings with tube attachments within the membrane surface are dispensed with; in this way, the properties of the membrane and the sealing of the membrane can be freely selected in a manner which is particularly functional and is independent of the inlet and outlet openings.

The autotransfusion apparatus of the invention can also be used when blood is removed from one patient and directly fed to another patient.

The membrane can be welded between the bottom and cover parts of the bottle or have a thickened rim as a mounting seat which is detachably clamped within an annular groove between the bottom and cover parts by a threaded closure. According to another embodiment of the invention, the screen, instead of being welded or adhered in the cover, can also be held detachably in a groove in the cover. The clamping of the edge of the membrane has the advantage that the seal between the membrane and the container is not subject to the pressure prevailing in the bottom space or cover space so that there is no danger of pressure or vacuum exerted reducing the tightness between the edge of the membrane and the container.

In accordance with another embodiment of the invention an inflatable balloon may be used as the membrane, the mouth of which is held hermetically fast against the rim of the opening in the bottom part for the gas pressure which is different from the inside of the container. The balloon is suitably fixed to the container bottom.

Together with the blood which is drawn in, foam and fat particles frequently also enter into the cover space, for which reason the screen is preferably arranged spaced from the outlet opening within the container. In this way, the result is, on the one hand, that upon the use of compressed air the membrane can be pressed only until it rests against the screen and can therefore not be damaged in the outlet opening. On the other hand, after turning the container over and when the outlet opening, therefore, faces down, a residual quantity of blood is retained between the screen and the outlet connection, the fat particles and the foam floating on the blood so that they can then be easily discarded.

By a suitably shaped suction connection the inlet opening, the body fluid is so introduced along the inner wall of the cover part and the membrane that it flows down atraumatically, which, in accordance with a further development of the invention, can be obtained by an inlet opening which opens tangentially to the inner wall of the cover part. This smooth introduction of the blood is provided where the inlet opening comprises a mouthpiece which widens in the manner of a trumpet or is of T-shape so that the flow of the blood entering the container is slowed down.

The autotransfusion apparatus of the invention assures the gentlest possible treatment for the blood to be transfused as well as for the patient. During the drawing-in of the blood, the air which is drawn in with it escapes through the vacuum connection arranged at the outlet opening and is not drawn in a traumatizing manner through the collected blood; this manner of use has the advantage over a vacuum connection in the bottom space—with which the traumatizing of the blood is also avoided—that larger quantities of entrained air do not reduce the blood receiving capacity of the autotransfusion apparatus. After the completion of the aspiration, any air which is still present in the cover space before the retransfusion, first of all, can be expelled by the introduction of pressure fluid into the bottom space, blood coagulum and coarse tissue particles being retained by the screen.

The container and the membrane can, independently of each other, be made of different elastic blood-friendly compatible materials such as polyurethane, polyvinylchloride, silicone rubber, polyethylene, etc.

Of course, it is possible to introduce anti-coagulation liquids into the container without having to draw them in through the blood aspirator. For this reason, a two-way or three-way valve, arranged in front of the inlet opening, or another inlet opening in the cover part, may be employed. The three-way valve, or a T or Y piece in front of the inlet opening on the patient-side, furthermore permits simultaneous connection of two autotransfusion apparatus to the blood suction line so that the drawing off of blood can be effected either with increased suction power or continuoustly (without interruption), at least one autotransfusion apparatus being continuously connected to the suction line while the other apparatus can be clamped off after its capacity has been exhausted and replaced by a fresh apparatus.

With the autotransfusion apparatus of the invention it is therefore possible to satisfy simultaneously different important criteria, namely gentle aspiration, active retransfusion, retention of all coarse, injurious substances, retention of fat and foam, as well as possible reusability, together with a dependable and continuous readiness for operation.

Further details, features and advantages of the object of the invention will become evident from the following description of the accompanying drawings, which shows preferred embodiments of an autotransfusion apparatus according to the invention wherein:

DETAILED DESCRIPTION OF THE PREFERRED EMBODIMENTS

Figure 1:
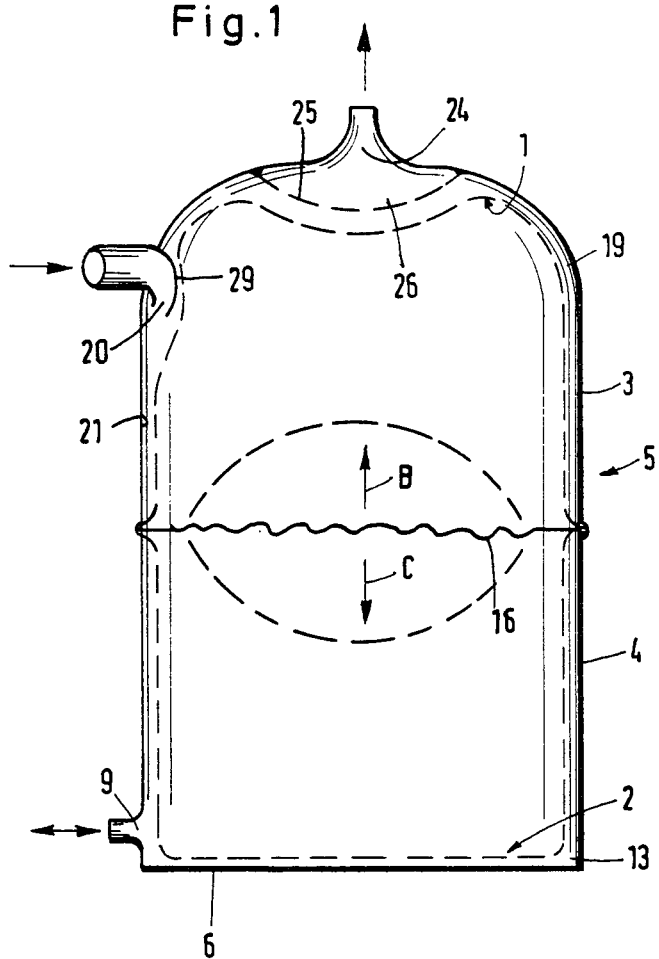
FIG. 1 is a longitudinal section through an autotransfusion apparatus.

FIG. 1 shows the essential part of an autotransfusion apparatus in the form of a container, designated generally as 5, which is made of sterilizable plastic or glass and can be formed as a disposable container. The container has a cylindrical or rectangular cross section and comprises a bottom part 4 and a cover part 3 which is connected in fluid-tight manner to the upper edge of said bottom part. The container 5 is resistant to vacuum and can be evacuated via an outlet opening 24 in the cover part 3 or an opening 9 in the bottom part 4. Within the cover part 3, at a sufficient distance from the outlet opening 24, an inlet opening 20 is arranged in the region of a trumpet-shaped mouthpiece 29 tangential to the inner wall 21 of the cover part 3 so that body fluid drawn in from the patient flows down along this inner wall by gravity, without the formation of foam. A screen 25 for retaining coarse substances entrained in the blood covers the outlet opening 24, spaced from the interior of the container. The opening 9 can be hermetically closed and after removal of the closure permits the entrance of atmospheric or compressed air into the inside of the container. A membrane 16 which is impervious to body fluid and is deformable by pressure has its edge so fixed hermetically between the bottom part 4 and the cover part 3 that it divides the container 5 into a gas-filled bottom space 13 and a cover space 19, sealed therefrom, to receive the body fluid. Under the influence of fluid pressure the membrane 16 can, as shown in dashed line, move substantially against the inner contour 1 of the cover part 3 and, alternatively, against the inner contour 2 of the bottom part 4. Of course, all intermediate positions of the membrane 16 between these two extreme positions can be assumed, as indicated by further dashed lines and the directional arrows B and C.

The connection between the edge of the membrane and the bottom and cover parts can be effected by plastic welding with the formation of a one-piece disposable container.

When the containers are completely full with blood, the membrane 16 assumes essentially the shape of the inner contour 2. The feed line from the patient is then tightly closed and possibly clamped off on the patient side. After the removal of a suction line (not shown), which is connected either to the outlet opening 24 or to the opening 9, the air still present in the cover space 3 and the following regions of the system can be expelled by the introduction of compressed air through the opening 9 and the connecting of a retransfusion fitting to the opening 24. The screen 25 serves to retain coarse particles. After the container 5 has been turned upside down, all the light substances of the blood, such as unexpelled air bubbles and fatty cells, collect after a period to come to rest below the membrane 16, which is then at the top. Upon the introduction then of atmospheric or compressed air through the opening 9, the blood flows back to the patient until the membrane 16 is applied completely against the contour 1 of the cover part 3 and against the screen 25. In this connection only coarse particles which have been retained by the screen remain between the membrane 16 and the screen 25 in the cover space 19, while fine components such as the afore-mentioned air bubbles or fat cells collect in concentrated manner in the space 26 between the outlet opening 24 and the screen 25 and can no longer reach the patient.

Figure 2:
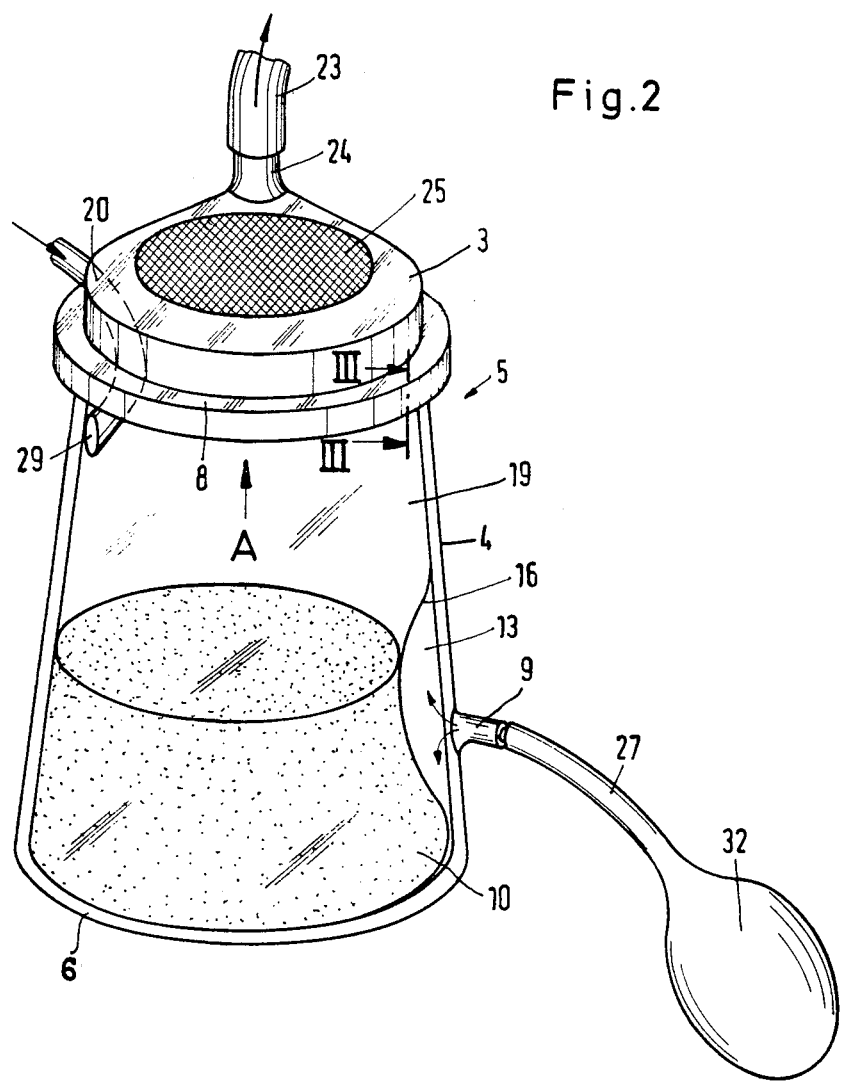
FIG. 2 is a view in perspective of another autotransfusion apparatus.

In accordance with FIG. 2, a reusable autotransfusion apparatus may have a widened base 6 (also possible in the case of FIG. 1) and a radially projecting threaded rim 7 on the open end of the bottom part 4 and a circumferential rim 8, corresponding thereto, on the open end of the cover part 3. In the center of the cover part 3, an outlet connector onto which a blood discharge tube 23 is placed has the outlet opening 24. In the vicinity of the rim 8, an inlet connector having an inlet opening 20 to which reference will be had further below, extends through the cover part 3. The inner surface of the cover part 3 has an annular shoulder into which a disk-shaped screen 25 is inserted. The shoulder is developed in such a manner that the screen is held in a clamped fit in the cover part 3 and can be replaced if necessary. For simpler handling, a handle 30 (FIG. 4) is formed on the screen 25. Between the rim 9 and the threaded edge 7, the rim (edge bead) 15 of a thin membrane 16 is clamped in such a manner (see in detail FIG. 3), that the membrane 16 hangs free in the shape of a bag within the bottom part 4. The membrane 16 consists of soft, for instance rubber-like, sterilizable material, the shape of which readily yields to the action of pressure. A closure cap can be placed over a connector nipple at the opening 9 of the bottom part 4; the closure cap can be removed and replaced by a pressure tube 27 extending from a pressure source 32 having the form of a manually actuated bulb.

Figure 3:
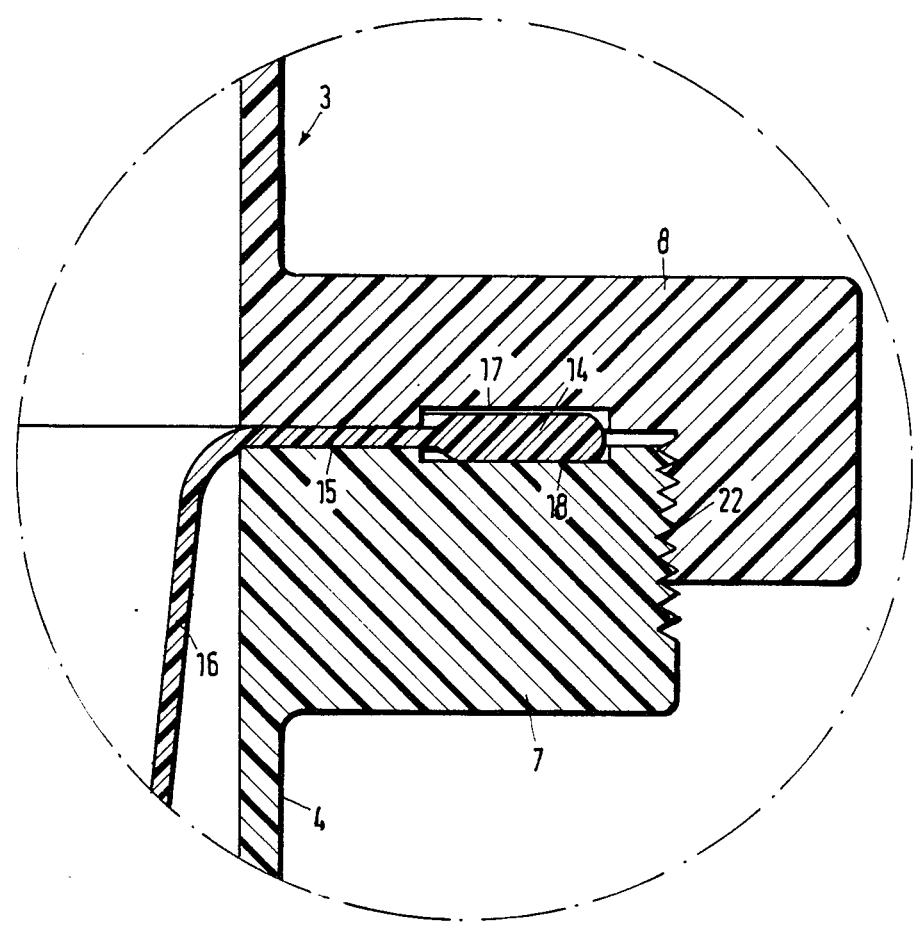
FIG. 3 shows the same autotransfusion apparatus in longitudinal section along the line III—III of FIG. 2 on a larger scale.
Figure 4:
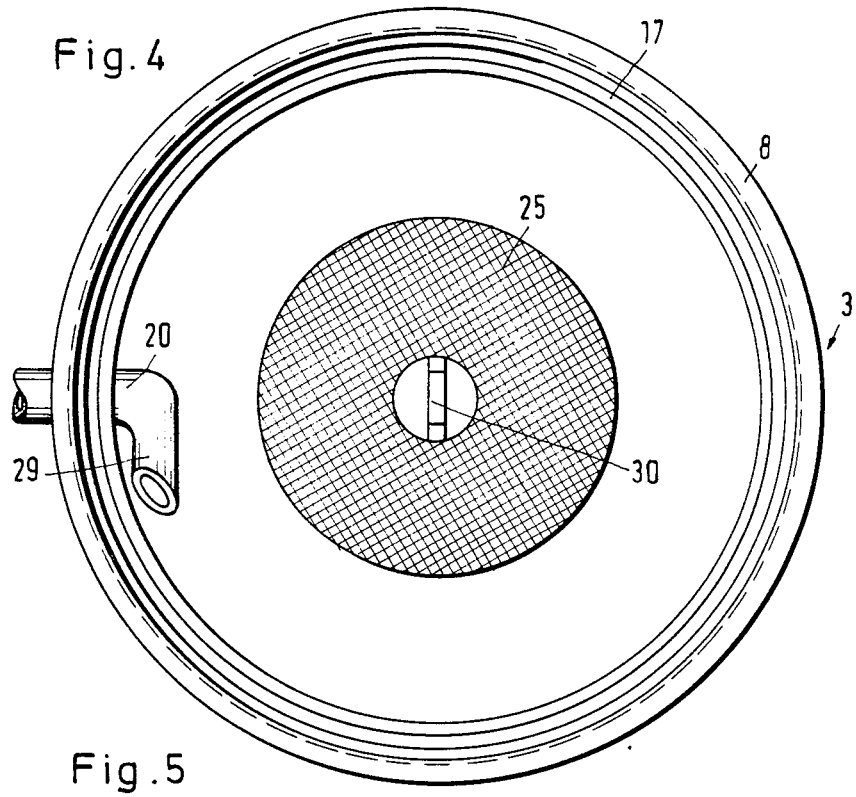
FIG. 4 shows the same autotransfusion apparatus in the inside view A indicated in FIG. 2.

In accordance with the detail showing of FIG. 3, the cover part 3 has a circumferentially projecting rim 8 which is provided with a thread 22 on its outer downwardly bent end. The circumferentially projecting threaded rim 7 of the bottom part 4 is provided on its outer surface with a corresponding screw threaded so that the cover part 3 can be screwed onto the bottom part 4 and removed from it in order to replace the membrane 16. The rim 8 is provided on its downwardly facing surface with an annular groove 17 and in the embodiment shown the upwardly-directed surface of the threaded rim 7 is provided with a facing annular groove 18. The edge 14 of the membrane 16 is thickened in such a manner that it is held securely in the space defined by the annular grooves when the cover part 3 is screwed onto the bottom part 4.

As shown particularly clearly in FIG. 3, the section of the edge 15 of the membrane 16 which adjoins the thickened rim 14 is clamped between the rim 8 and the threaded rim 7 when the cover part is screwed onto the bottom part. This manner of anchoring the edge of the membrane on the container 5 has the particular advantage that the positive pressure in the bottom space 13 which is applied to press the blood 10 (FIG. 2) out of the cover space 19 has no influence on the tightness of the clamping of the edge section 15 of the membrane 16. In this way assurance is had that the bottom space 13 will always remain hermetically sealed off from the cover space 19. The function of the autotransfusion apparatus of FIG. 2 corresponds otherwise to the function described in connection with FIG. 1, it now being possible, after retransfusion has been effected, to take apart, clean and sterilize or replace the four principal structural groups (bottom part, cover part, screen and membrane) so that repeated use is possible.

The bottom part 4 may, in the extreme case, have the shape of a bottle-like container with a relatively small cover opening, a relatively small cover part 3 securing at its edge a bag-shaped membrane 16 on the edge of the opening of the bottom part 4 and necessarily having an inlet opening as well as an outlet opening provided with screen.

Figure 5:
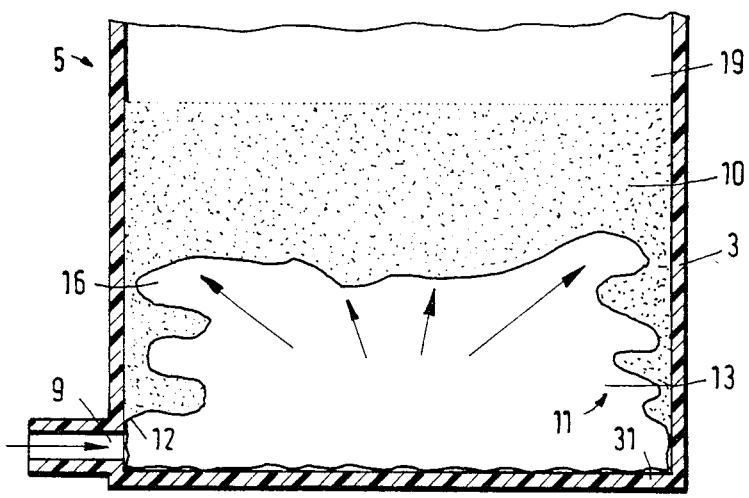
FIG. 5 is a partial view in longitudinal section of another autotransfusion apparatus.

FIG. 5 shows another embodiment of the invention in which the membrane 16 has the shape of an inflatable balloon 11. The balloon 11 is fixed in some suitable manner, for instance by adhesion, to the bottom 31 of the container 5. The edge 12 of the mouth of the inflatable balloon 11 is fastened hermetically all around in the opening 9 which is close to the bottom. For this purpose the edge 12 of the mouth can be placed around a connection nipple for the opening 9 and be held by a plug cap or the like. In this way, the bottom part is reduced to this plug cap, in the same way as the cover part (as mentioned above) can also be reduced to a very small region of the container 5.

The danger of traumatizing the blood 10 upon introduction into the container 5 is avoided (as already explained in connection with FIG. 1) by a suitable shaping of the inlet opening 20 with the mouthpiece 29.

I claim:

1. An autotransfusion apparatus for body fluid including blood, comprising
    an evacuatable vacuum-resistant container defining an inside for the body fluid and having a bottom part and a cover part,
    said cover part having means comprising an inlet opening into the inside of the container for the body fluid,
    said cover part having means comprising an outlet opening from the inside of the container for the body fluid,
    a screen covering said outlet opening,
    means comprising another opening in said container for producing a gas-flow connection to space within the container having a gas pressure which differs from pressure in said inside of the container,
    said another opening is arranged in the bottom part,
    a membrane which is deformable by pressure and impervious to the body fluid being fixed hermetically at an edge of the membrane between said bottom part and said cover part,
    said membrane dividing the container into the space forming a gas-fillable bottom space and a cover space defining said inside for the body fluid sealed from each other, said cover space communicating with said inlet and outlet openings, and
    said membrane being deformable under the influence of fluid pressure, substantially against an inner contour of said cover part and against an inner contour of said bottom part, respectively.

2. The apparatus according to claim 1, wherein said container is formed together with said membrane as a disposable one-piece container.

3. The apparatus according to claim 1, wherein said cover part is detachably fastened to said bottom part.

4. The apparatus according to claim 3, wherein said cover part is screwed to said bottom part.

5. The apparatus according to claim 3, wherein said edge includes an edge section of the membrane, said edge section is clamped between said cover part and said bottom part.

6. The apparatus according to claim 5, wherein said cover part has a rim formed with an annular groove,
    said edge section forms a thickened edge of the membrane,
    said thickened edge is hermetically held in said annular groove of said rim of said cover.

7. An autotransfusion apparatus for body fluid including blood, comprising
    an evacuatable vacuum-resistant container defining an inside for the body fluid and having a bottom part and a cover part,
    said cover part having means comprising an inlet opening into the inside of the container for the body fluid,
    said cover part having means comprising an outlet opening from the inside of the container for the body fluid,
    a screen covering said outlet opening, means comprising another opening in said container for producing a gas-flow connection to space within the container having a gas pressure which differs from pressure in said inside of the container, said another opening is arranged in the bottom part, a membrane which is deformable by pressure and impervious to the body fluid comprising an inflatable balloon secured hermetically with a mouth rim of the balloon against an edge of said another opening, said membrane dividing the container into the space forming a gas-fillable bottom space and a cover space defining said inside for the body fluid sealed from each other, said cover space communicating with said inlet and outlet openings, and said membrane being deformable under the influence of fluid pressure, substantially against an inner contour of said cover part and against an inner contour of said bottom part, respectively.

8. The apparatus according to claim 1, wherein said inlet opening opens tangentially to an inner wall of said cover part.

9. The apparatus according to claim 8, wherein said means comprising said inlet opening comprises a T-shaped mouthpiece.

10. The apparatus according to claim 8, wherein said means comprising said inlet opening comprises a mouthpiece which widens in trumpet shape.

11. The apparatus according to claim 1, wherein said screen is mounted in said cover part at a distance in front of said outlet opening and defines a space between said screen and said outlet opening for retaining substances floating on the body fluid which are carried along through the screen.

12. The apparatus according to claim 11, wherein said screen is detachably mounted in said cover part.

13. The apparatus according to claim 2, wherein said container is made of plastic.

14. An autotransfusion apparatus for body fluid including blood, comprising an evacuatable vacuum-resistant container defining an inside for the body fluid and having a bottom part and a cover part, said cover part having means comprising an inlet opening into the inside of the container for the body fluid, said cover part having means comprising an outlet opening from the inside of the container for the body fluid, a screen covering said outlet opening, means comprising another opening in said container for producing a gas-flow connection to space within the container having a gas pressure which differs from pressure in said inside of the container, said another opening is arranged in the bottom part, a membrane which is deformable by pressure and impervious to the body fluid hermetically dividing the container into the space forming a gas-fillable bottom space and a cover space defining said inside for the body fluid sealed from each other, said cover space communicating with said inlet and outlet openings, and said membrane being deformable under the influence of fluid pressure, substantially against an inner contour of said cover part and against an inner contour of said bottom part, respectively.

15. The apparatus according to claim 1, wherein said membrane is continuous without openings.

16. The apparatus according to claim 14, wherein said membrane is continuous without openings.

17. The apparatus according to claim 7, wherein said membrane is continuous without openings other than said mouth rim.

18. The apparatus according to claim 1, wherein said container defines a single chamber.

19. The apparatus according to claim 7, wherein said container defines a single chamber.

20. The apparatus according to claim 14, wherein said container defines a single chamber.

* * * * *